United States Patent [19]

Grasselli et al.

[11] 4,167,494

[45] Sep. 11, 1979

[54] PRODUCTION OF UNSATURATED NITRILES USING CATALYSTS CONTAINING BORON, GALLIUM OR INDIUM

[75] Inventors: Robert K. Grasselli, Chagrin Falls; Dev D. Suresh, Macedonia; Arthur F. Miller, Lyndhurst, all of Ohio

[73] Assignee: The Standard Oil Company, Cleveland, Ohio

[21] Appl. No.: 821,035

[22] Filed: Aug. 21, 1977

[51] Int. Cl.² .................. B01J 21/02; B01J 27/14; B01J 27/02; B01J 23/10
[52] U.S. Cl. .................... 252/432; 252/435; 252/437; 252/439; 252/462; 252/464; 252/465; 252/466 J; 260/465.3
[58] Field of Search .................. 252/465, 466 J, 432, 252/462, 464, 435, 437, 439

[56] References Cited

U.S. PATENT DOCUMENTS

| 3,522,299 | 7/1970 | Takenaka | 252/437 X |
|---|---|---|---|
| 3,576,764 | 4/1971 | Yamaguchi | 252/437 |
| 3,764,632 | 10/1973 | Takenaka et al. | 252/437 X |
| 3,786,000 | 1/1974 | Ono et al. | 252/466 J X |
| 3,803,204 | 4/1974 | Grasselli et al. | 252/432 X |
| 3,972,920 | 8/1976 | Ishii et al. | 252/469 X |
| 4,001,317 | 1/1977 | Grasselli et al. | 252/462 X |
| 4,035,418 | 7/1977 | Okada et al. | 252/469 X |
| 4,052,450 | 10/1977 | Krabetz et al. | 252/437 X |

*Primary Examiner*—Delbert E. Gantz
*Assistant Examiner*—William G. Wright
*Attorney, Agent, or Firm*—John E. Miller, Jr.; Herbert D. Knudsen; Larry W. Evans

[57] ABSTRACT

Certain catalysts containing iron and molybdenum plus bismuth or tellurium and nickel, cobalt, manganese, magnesium, zinc, cadmium, calcium or beryllium have been found to give especially large volumes of acrylonitrile or methacrylonitrile in a given time when boron, gallium or indium are incorporated into the catalyst.

8 Claims, No Drawings

PRODUCTION OF UNSATURATED NITRILES USING CATALYSTS CONTAINING BORON, GALLIUM OR INDIUM

BACKGROUND OF THE INVENTION

U.S. Pat. No. 3,354,197 shows certain catalysts that contain boron. The use of boron, however, in the particular catalysts of the present invention are the especially high through-put at high per pass conversions made possible by the catalysts of the present invention could not have been predicted from the art.

A number of very desirable ammoxidation catalysts are known which represent the base catalysts of the invention. These catalysts are used to produce acrylonitrile or methacrylonitrile under certain conditions with high per pass conversions. Under these conditions, if the amount of olefin fed over the catalyst in a given time is increased significantly, the per pass conversion tends to drop. In some instances, the per pass conversion to unsaturated nitriles drops markedly. Since the viability of a commercial operation is significantly affected by the amount of product that can be prepared in a given time, the present invention is directed at the problem in the art of increasing the production of product in a given time while maintaining high per pass conversions.

SUMMARY OF THE INVENTION

It has now been discovered in the process for the preparation of acrylonitrile or methacrylonitrile by the reaction of propylene or isobutylene, molecular oxygen and ammonia at a temperature of about 200° C. to about 600° C. in the presence of an oxidation catalyst, the improvement comprising using as the oxidation catalyst a catalyst having the atomic ratios described by the formula $$X_a A_b C_c Fe_d D_e Mo_{12} O_x$$

wherein
X is B, Ga, In or mixture thereof;
A is an alkali metal, alkaline earth metal, rare earth metal, Nb, Ta, Tl, P, As, Sb, W or mixture thereof;
C is Ni, Co, Mg, Mn, Zn, Cd, Ca, Be or mixture thereof;
D is Bi, Te or mixture thereof;
and wherein
a is 0.01 to about 4;
b is 0 to about 4;
c and d are 0.01 to about 12;
e is 0.01 to about 6; and
x is the number of oxygens required to satisfy the valence requirements of the other elements present.

The process of the present invention provides a commercially feasible process for preparing large quantities of acrylonitrile or methacrylonitrile in a given period of time at high per pass conversions.

The amount of a desirable acrylonitrile or methacrylonitrile produced in an ammoxidation reaction is essentially a function of (1) the amount of olefin fed to the reactor in a given period of time, and (2) the per pass conversion to the product. As noted above, catalysts useful in ammoxidation reactions have been limited to a certain range of feed rates to provide high per pass conversions. When higher feed rates are attempted, the per pass conversion drops and the reaction becomes inefficient. At very high per pass conversions, the feed rate is so slow that the production rate suffers. The present invention solves this problem by the discovery of catalysts that can accept a high reactant feed rate while at the same time maintain a high per pass conversion.

The reactant feed rate is normally stated as "WWH" and is measured according to the following formula:

$$WWH = \frac{\text{weight of olefin fed}}{\text{weight of catalyst} \times \text{hours}}$$

It can be seen from the formula that the rate of reactant feed varies directly with the WWH—as the WWH increases, the rate of reactant feed increases.

The second variable is the per pass conversion. Per pass conversion is usually stated in terms of mole percent according to the following formula for acrylonitrile.

$$\text{Mole \%}_{\text{p.p.c.}} = \frac{\text{moles of acrylonitrile in reactor effluent}}{\text{moles of olefin fed}} \times 100$$

It is seen that the amount of product formed is a direct function of the per pass conversion.

The central aspect of the present invention is the catalyst employed. The catalyst is suitably any catalyst containing the elements described in the formula above. Broadly, the base catalysts contain at least iron and molybdenum and bismuth or tellurium and at least one of nickel, cobalt, magnesium, manganese, zinc, cadmium, calcium or beryllium. In addition to these base elements, there is a large number of optional elements that could be incorporated into the catalyst. The base catalysts of the invention are known catalysts useful for ammoxidation reactions. Accordingly, the base catalyst and its preparations are not the subject of the present invention even though there are preferred variations in the base catalyst.

The present invention is the incorporation of boron, gallium, indium or mixture thereof into the base catalyst to provide higher rates of the production at high per pass conversions.

The boron, gallium or indium can be incorporated into the catalyst by any of the techniques that are employed to produce the base catalyst. A preferred method is coprecipitating a soluble compound of the element in the formation of the catalytic matrix. A preferred method of accomplishing these preparations is shown in the Specific Embodiments.

The boron, gallium and indium can be incorporated into the catalysts in any amount that is effective to obtain improved results of the present invention. Although this range may vary, a preferred range of 0.01 to about 4 is designated in the general formula. A more preferred range is about 0.1 to about 3.

Although a mixture of boron, gallium and indium could be used, it is preferred to use each of these elements separately in the catalyst. In the catalyst formula, this is accomplished by separately setting X equal each of these elements.

The base catalyst to which the boron, gallium or indium is added also has preferred embodiments. Preffered are catalysts that contain bismuth, i.e. where D is bismuth. Also preferred are catalysts that contain nickel or cobalt or mixtures thereof, i.e., wherein C is nickel, cobalt or mixtures thereof.

The catalysts of the invention are suitably used in supported or unsupported form. Representative examples of carrier materials include silica, alumina, zirconia, titanium dioxide, boron phosphate and the like.

The reactants, process conditions and other reaction parameters of the reaction are known in the art of the ammoxidation of propylene and isobutylene. The conditions, reactors and the like are not substantially changed from the art. The temperature may range from about 200° to about 600° C. with about 300° to about 500° C. being preferred. The reaction may be conducted in a fluid or a fixed-bed reactor using atmospheric, subatmospheric or superatmospheric pressure. A feasible commercial application could be used of the present invention in a fluidized-bed reactor at superatmospheric pressure.

Since the present invention is primarily designed to feed more olefin over a catalyst in a given time, it is understood that the feed rates and composition of the feed could be altered from the art. Expressed in terms of WWH, the feed of olefin over the catalyst is preferably between about 0.05 and about 0.25.

Using the present invention, large quantities of acrylonitrile or methacrylonitrile are produced at high olefin feed rates and high per pass conversions.

SPECIFIC EMBODIMENTS

Comparative Examples A & B and Examples 1–6 — Comparison of catalyst containing boron, gallium or indium with base catalyst A 5 cc. fixed-bed reactor was constructed of a 8 mm. inside diameter stainless steel tube. Catalyst prepared as described below were charged to the reactor and heated to 420° C. under a flow of air. At the reaction temperature for Comparative Example B and Examples 1–6, a reactant composition of propylene/ammonia/oxygen/nitrogen/steam of 1.8/2.2/3.6/2.4/6 was fed over the catalyst at a contact time of 3 seconds. The WWH for the reaction was 0.10.

For Comparative Example A, a reactant feed of propylene/ammonia/air/steam in the ratio 1/1.1/10/4 was used at a temperature of 420° C. A contact time of 6 seconds was used. The WWH was 0.03. This example is included to show a base catalyst operating under normal operating conditions at a low WWH.

The catalysts were prepared as follows:

Comparative Examples A and B

80% $K_{0.1}Ni_{2.5}Co_{4.5}Fe_3BiP_{0.5}Mo_{12}O_x$ + 20% $SiO_2$

A solution of 127.1 g. ammonium heptamolybdate $(NH_4)_6Mo_7O_{24}.4H_2O$ and water was prepared. To this solution was added 6.9 g. of a 42.5% solution of $H_3PO_4$ and 102.7g. of Nalco 40% silica sol to form a slurry. Separately, an aqueous solution containing 72.7 g., ferric nitrate, $Fe(NO_3)_3.9H_2O$; 29.1 g. bismuth nitrate, $Bi(NO_3)_3.5H_2O$; 78.6 g. cobalt nitrate $Co(NO_3)_2.6H_2O$; 43.6 g. nickel nitrate, $Ni(NO_3)_2.6H_2O$; and 6.1 g. of a 10% potassium nitrate solution was prepared. The solution of metal nitrates was slowly added to the slurry. The resulting slurry was evaporated to dryness, and the solid obtained was heat treated at 290° C. for three hours, at 425° C. for three hours and at 550° C. for 16 hours.

EXAMPLE 1

80% $B_{0.5}K_{0.1}Ni_{2.5}Co_{4.5}Fe_3BiMo_{12}O_x$ + 20% $SiO_2$

The catalyst was prepared in the same manner as Comparative Examples A and B except that a half recipe was used, 0.93 g. $H_3BO_3$ was added to the molybdenum solution and no phosphoric acid was added.

EXAMPLE 2

80% $B_{1.0}K_{0.1}Ni_{2.5}Co_{4.5}Fe_3BiP_{0.5}Mo_{12}O_x$ + 20% $SiO_2$

This catalyst was prepared in exactly the same way as Comparative Examples A and B except that a half recipe was used and 1.86 g. $H_3BO_3$ was added to the metal nitrate solution.

EXAMPLE 3

80% $Ga_{1.0}K_{0.1}Ni_{2.5}Co_{4.5}Fe_3BiP_{0.5}Mo_{14}O_x$ + 20% $SiO_2$

In the same manner as described in the examples above, a catalyst was prepared using a first slurry containing 24.7 g. ammonium heptamolydate, 19.4 g. Nalco 40% silica and 1.15 g. of a 42.5% solution of $H_3PO_4$. The second slurry contained 12.1 g. ferric nitrate, 4.8 g. bismuth nitrate, 13.1 g. cobalt nitrate, 7.3 g. nickel nitrate, 1.0 g. of a 10% solution of potassium nitrate and 2.5 g. of gallium nitrate, $Ga(NO_3)_3.3H_2O$. The slurries were combined, evaporated and heat treated as shown above.

EXAMPLE 4

80% $In_{1.0}K_{0.1}Ni_{2.5}Co_{4.5}Fe_3BiP_{0.5}Mo_{13.5}O_x$ + 20% $SiO_2$

A first slurry containing 71.6 g. ammonium heptamolybdate, 58.0 g. of Nalco 40% silica sol and 3.4 g. of a 42.5% solution of phosphoric acid was prepared. A second slurry containing 36.4 g. of ferric nitrate, 14.6 g. bismuth nitrate, 39.3 g. cobalt nitrate, 21.8 g. nickel nitrate, 3.0 g. of a 10% solution of potassium nitrate and 4.5 g. of indium chloride was prepared. The slurries were combined, and the solid catalyst was heat treated as described above.

EXAMPLE 5

80% $B_{2.4}W_{0.6}K_{0.1}Ni_{2.5}Co_{4.5}Fe_3BiP_{0.5}Mo_{10.8}O_x$ + 20% $SiO_2$

A slurry of 57.2 g. ammonium heptamolybdate, 4.8 g. ammonium heptatungslate, $(NH_4)_6W_7O_{24}.6H_2O$, 4.5 g. boric acid, 3.5 g. of a 42.5% solution of phosphoric acid and 52.3 g. of Nalco 40% silica sol was prepared. To this slurry was added a solution of 36.4 g. ferric nitrate, 14.6 g. bismuth nitrate, 39.3 cobalt nitrate, 21.8 g. nickel nitrate and 3.0 g. of a 10% solution of potassium nitrate. The resulting slurry was evaporated and the solid was heat treated as described above.

EXAMPLE 6

80% $B_{1.0}K_{0.1}Ni_{2.5}Co_{4.5}Fe_3BiP_{0.5}Mo_{12}O_x$ + 20% $SiO_2$ (Aerosil)

This catalyst was prepared in exactly the same way as the catalyst of Example 2 except that Aerosil silica was used instead of Nalco 40% silica sol.

The results of ammoxidation experiments to obtain arcylonitrile are shown in Table I.

Table I

Preparation of Acrylonitrile
Comparison of Catalysts of the Invention
With Base Catalyst

| Example | Active Ingredients of Catalyst | Molar Per Pass Conversion % |
|---|---|---|
| Comp. A | $K_{0.1}Ni_{2.5}Co_{4.5}Fe_3BiP_{0.5}Mo_{12}O_x$ | 80.1 |
| Comp. B | " | 73.1 |
| 1 | $B_{0.5}K_{0.1}Ni_{2.5}Co_{4.5}Fe_3BiMo_{12}O_x$ | 76.5 |
| 2 | $B_{1.0}K_{0.1}Ni_{2.5}Co_{4.5}Fe_3BiP_{0.5}Mo_{12}O_x$ | 80.4 |
| 3 | $Ga_{1.0}K_{0.1}Ni_{2.5}Co_{4.5}Fe_3BiP_{0.5}Mo_{14}O_x$ | 76.1 |
| 4 | $In_{1.0}K_{0.1}Ni_{2.5}Co_{4.5}Fe_3BiP_{0.5}Mo_{13.5}O_x$ | 76.1 |
| 5 | $B_{2.4}W_{0.6}K_{0.1}Ni_{2.5}Co_{4.5}Fe_3BiP_{0.5}Mo_{10.8}O_x$ | 75.7 |
| 6 | $B_{1.0}K_{0.1}Ni_{2.5}Co_{4.5}Fe_3BiP_{0.5}Mo_{12}O_x$ | 82.8 |

It can be seen from the data in Table I that under normal conditions of a WWH of about 0.03, the base catalyst gives high per pass conversions. As the WWH is increased to 0.10, the per pass conversion drops off significantly. Examples 1-6 of the invention demonstrate how the higher per pass conversions are at least partially restored by the catalysts of the invention.

In the same manner as shown by the examples above, the catalysts of the invention are used in the ammoxidation of isobutylene to obtain methacrylonitrile. Also, in the same manner other catalysts described by the general formula are prepared and exhibit a retention of the high per pass conversions at high WWH.

We claim:

1. A catalyst having the atomic ratios described by the formula:

$$X_aA_bC_cFe_dD_eMo_{12}O_x$$

wherein
X is Ga, In or mixture thereof;
A is an alkali metal, Sr, Ba, Ra, rare earth metal, Nb, Ta, Tl, P, As, Sb, W or mixture thereof;
C is Ni, Co, Mg, Zn, Cd, Ca, Be or mixture thereof;
D is Bi, Te or mixture thereof;
and wherein
a is 0.01 to about 4;
b is 0 to about 4;
c and d are 0.01 to about 12;
e is 0.01 to about 6; and
x is the number of oxygens required to satisfy the valence requirements of the other elements present,
said catalyst being free of tin.

2. The catalyst of claim 1 wherein a is about 0.01 to about 3.
3. The catalyst of claim 1 wherein X is indium.
4. The catalyst of claim 1 wherein C is nickel, cobalt or mixtures thereof.
5. The catalyst of claim 1 wherein D is bismuth.
6. A catalyst having the atomic ratios described by the formula:

$$X_aA_bC_cFe_dD_eMo_{12}O_x$$

wherein
X is B, Ga, In or mixture thereof;
C is Ni, Co, Mg, Zn, Cd, Ca, Be or mixtures thereof
A is a rare earth metal, Nb, Ta, or mixtures thereof;
D is Bi, Te or mixture thereof;
and wherein
a is 0.01 to about 4;
b is 0 to about 4;
c and d are 0.01 to about 12;
e is 0.01 to about 6; and
x is the number of oxygens required to satisfy the valence requirements of the other elements present,
said catalyst being free of tin, said catalyst further being free of Sb when x is B.

7. The catalyst of claim 6 wherein X is B.
8. A catalyst having the atomic ratios described by the formula:

$$Ga_aA_bC_cFe_dD_eMo_{12}O_x$$

wherein
A is an alkali metal, Sr, Ba, Ra, rare earth metal, Nb, Ta, Tl, P, As, Sb, W or mixture thereof;
C is Ni, Co, Mg, Zn, Cd, Ca, Be, or mixture thereof;
D is Bi, Te or mixture thereof;
and wherein
a is 0.01 to about 4;
b is 0 to about 4;
c and d are 0.01 to about 12;
e is 0.01 to about 6; and
x is the number of oxygens required to satisfy the valence requirements of the other elements present.

* * * * *